United States Patent [19]

Arata et al.

[11] Patent Number: 4,844,068
[45] Date of Patent: Jul. 4, 1989

[54] BARIATRIC SURGICAL INSTRUMENT

[75] Inventors: Justin E. Arata, Ft. Wayne, Ind.; John N. Pynn, Whitehouse, N.J.

[73] Assignee: Ethicon, Inc., Somerville, N.J.

[21] Appl. No.: 58,303

[22] Filed: Jun. 5, 1987

[51] Int. Cl.⁴ .................. A61B 17/28; A61B 17/08
[52] U.S. Cl. ........................... 128/346; 128/326
[58] Field of Search .......... 128/326, 321, 346, 334 R, 128/305, 334

[56] References Cited

U.S. PATENT DOCUMENTS

| | | | |
|---|---|---|---|
| Re. 20,201 | 12/1936 | Sivon | 128/346 |
| 2,705,958 | 4/1955 | Akl | 128/346 |
| 3,786,815 | 1/1974 | Ericson | 128/346 |
| 3,926,195 | 12/1975 | Bleier | 128/346 |
| 4,558,699 | 12/1985 | Bashour | 128/346 |
| 4,624,255 | 11/1986 | Schenck | 128/346 |
| 4,665,917 | 5/1987 | Clanton | 128/346 |

FOREIGN PATENT DOCUMENTS 0105414  4/1984  European Pat. Off. ............ 128/346

Primary Examiner—Carl Stuart Miller

[57] ABSTRACT

A surgical instrument useful for forming a buttonhole through the stomach walls in gastroplastic surgery has a forceps handle, a hinge, and two jaws. The jaws form an aperture proximal the hinge which grasps the tubular pouch formed along the stomach wall. At the distal end of the jaws are a pair of rings which compress and define the location of a stapled buttonhole in the stomach walls. A cup is attached to one ring which is adapted to hold the nut and anvil of a stapling device which is used to cut the buttonhole in the center of the compressed rings and to affix a ring of staples about the periphery of the buttonhole.

10 Claims, 2 Drawing Sheets

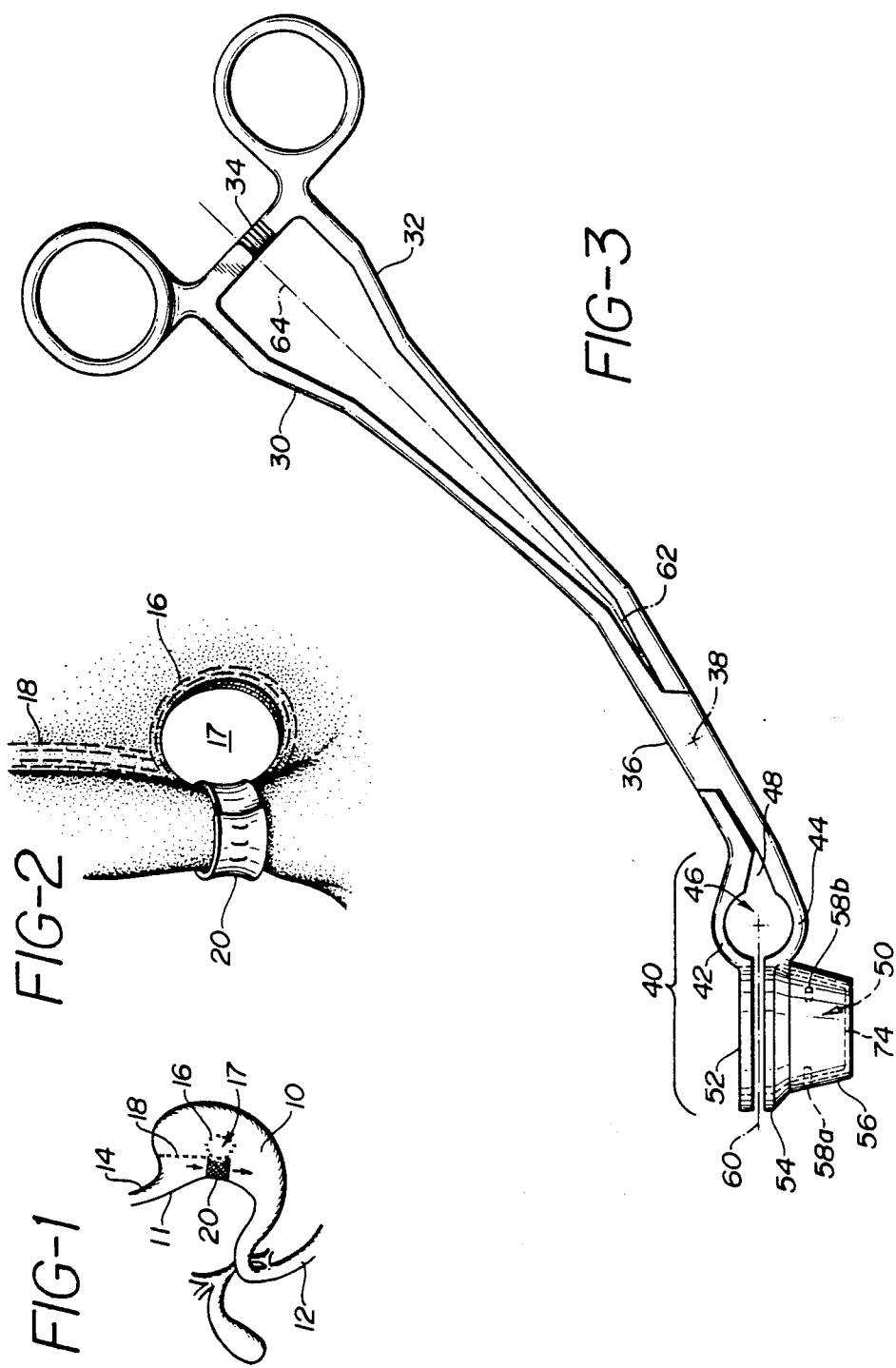

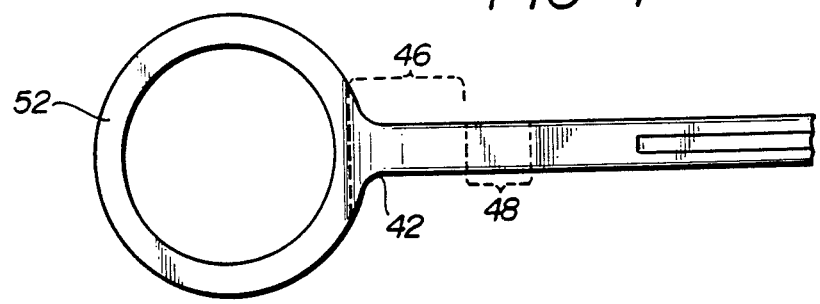
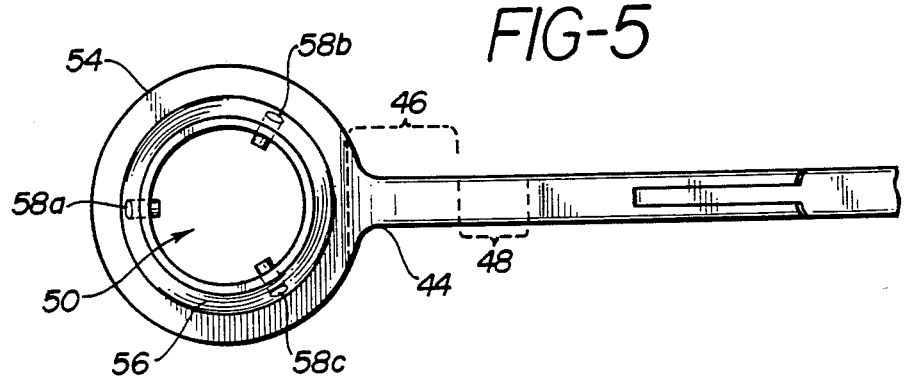
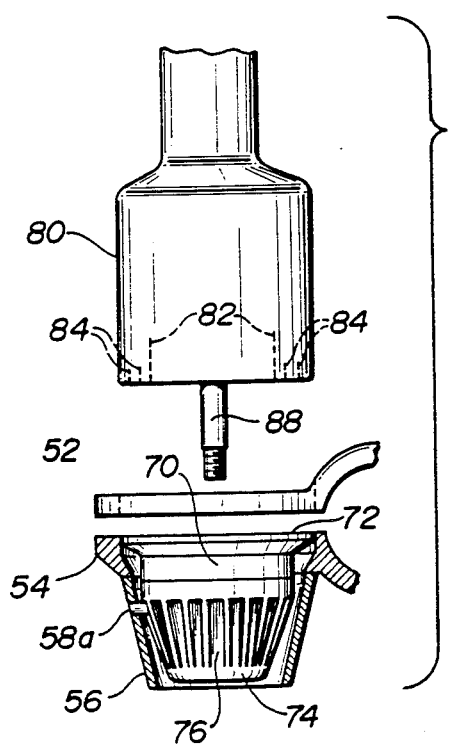
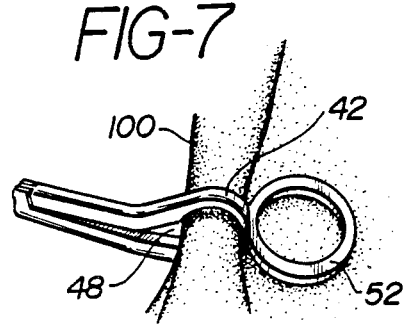

BARIATRIC SURGICAL INSTRUMENT

This invention relates to surgical instruments useful in bariatric surgery and, in particular, to procedures and apparatus useful in the treatment of morbid obesity.

Morbid obesity is a serious malady which has been the subject of many forms of treatment. A person is considered to be morbidly obese if he is at least 50% over his ideal body weight, is double his body weight, or is 100 pounds over his ideal weight. The term "morbid" is used to describe the condition because serious, often life-threatening symptoms such as diabetes, hypertension, coronary artery disease and arteriosclerosis generally accompany the condition, and their occurrence can be lessened with dramatic weight loss.

Numerous non-operative therapies for morbid obesity have been tried with virtually no permanent success. Dietary counseling, behavior modification, wiring a patient's jaws shut, and pharmacologic methods have all been tried, and failed to correct the condition. Mechanical apparatus for insertion into the body through non-surgical means, such as the use of esophago-gastric balloons to fill the stomach have also been employed in the treatment of the condition. Such devices cannot be employed over a long term, however, as they often cause severe irritation, necessitating their periodic removal and hence interruption of treatment. Thus, the medical community has evolved surgical approaches to treatment of morbid obesity.

Surgical procedures for treatment of morbid obesity may generally be classified as those directed toward the prevention of absorption of food and those directed toward the reduction of the intake of food. One of the first procedures employed was surgical bypass of a major portion of the jejunum and ileum, or small bowel bypass. This procedure was found to have significant complications, including liver disease and severe diarrhea. These complications led to replacement of the procedure by gastric bypass techniques. In variations of these techniques, the stomach is horizontally divided into two isolated pouches, with the upper pouch having a small food capacity. The upper pouch is connected to the small intestine through a small stoma, which restricts the processing of food by the greatly reduced useable stomach. However, it has been found that the small pouch and stoma can dilate over time, thereby reducing the long-term success of the procedure. The procedure has been accompanied by enough complications to stimulate further developments, including horizontal gastroplasty. Essentially, gastroplasty limits the intake of food by the creation of a small gastric pouch, and the emptying of the small pouch is delayed by limiting the size of the efferent stoma. Since gastroplasty, unlike the earlier bypass procedures, does not reroute portions of the gastrointestinal tract which vastly change its functioning, the gastroplasty procedures avoid many of the complications of bypass operations. In horizontal gastroplasty, the stomach is separated into two pouches by a horizontal row of staples. The row of staples is interrupted to provide a small stoma between the two pouches. But again, dilatation of the stoma minimized long-term effectiveness, and the need to reinforce the stoma led to undesired complications from the intrusion of reinforcing material into the gastric lumen.

These considerations led to the development of vertical banded gastroplasty. This procedure overcomes the stoma-related problems of horizontal gastroplasty by externally surrounding the efferent stoma with a prosthesis or collar of reinforcing material, such as Silastic tubing or Marlex mesh. The reinforcing collar prevents dilatation of the efferent stoma over time because it completely and externally surrounds the stoma. Incidences of intrusion of the collar material into the lumen of the stomach are minimized by the formation of a buttonhole defining the size of the stoma where the collar passes through the posterior and anterior walls of the stomach.

The formation of the efferent stoma is a critical step in the procedure. The buttonhole which defines the stoma size must be precisely located. Formation of the buttonhole should not be done in a manner which permits gastric secretions to spill into the peritoneal cavity, leading to infection. The cutting and suturing of the buttonhole should be done quickly, easily and securely. Injury to nerves and blood vessels of the stomach wall should be avoided.

In accordance with the principles of the present invention, a surgical instrument is provided which enables the surgeon to achieve the above objectives during the vertical banded gastroplasty procedure. The instrument employs a forceps handle at its proximal end, an intermediate hinge, and clamping jaws at its distal end. The clamping jaws form an aperture proximal end, an intermediate hinge, and clamping jaws at its distal end. The clamping jaws form an aperture proximal the hinge, which encloses the stoma region to be defined by the procedure. At the distal end the jaws are formed into rings which provide several features. When the instrument is clamped on the stomach, the ring on the anterior wall of the stomach defines the location of the buttonhole. The ring on the posterior wall provides means for retaining suturing apparatus, such as the anvil of an intraluminal stapling instrument, facilitating rapid and easy formation and suturing of the buttonhole. The clamping action of the rings prevents leakage of gastric secretions into the peritoneal cavity.

In a preferred embodiment, the surgical instrument of the present invention includes a ratchet in the forceps handle for securing the instrument during use, and the jaws form an opening as a part of the stoma-defining aperture, which accommodates a portion of the stomach wall between the jaws. This opening allows the instrument to be closed securely without damaging nerves and blood vessels in the stomach wall.

In the drawings:

FIG. 1 is a schematic drawing showing major features of vertical banded gastroplasty;

FIG. 2 is a detailed view of the collar and buttonhole of FIG. 1;

FIG. 3 is a side view of the surgical instrument of the present invention;

FIG. 4 is a top view of the upper jaw of the surgical instrument of FIG. 3;

FIG. 5 is a bottom view of the lower jaw of the surgical instrument of FIG. 4;

FIG. 6 is a side view of the distal end of the surgical instrument of FIG. 1 with a stapler nut and anvil located in the cup; and FIG. 7 illustrates the clamped jaws of the surgical instrument of the present invention when positioned during a vertical banded gastroplasty procedure.

Referring first to FIG. 1, the principal features of a vertical banded gastroplasty procedure are shown. A stomach 10 is represented, joined at the top to the esophagus 14 and at the bottom to the small intestine 12. The steps of the procedure are to first form a buttonhole 17 through both walls of the stomach. The buttonhole 17 is closed about its periphery by a circular pattern of staples 16. Next, lines of staples 18 are put in place to define the small pouch along the lesser curvature 11 of the stomach. Finally, the collar or band 20 is secured around the efferent stoma at the bottom of the small pouch.

FIG. 2 is a more detailed view of the efferent stoma region at the bottom of the small pouch. The band 20, which may have a circumference of 5 cm. for instance, is seen to pass through the buttonhole 17 as it surrounds the efferent stoma of the small pouch, thereby preventing any dilatation of the stoma.

A surgical instrument constructed in accordance with the principles of the present invention is shown in FIG. 3. The instrument comprises two arms which are joined at a pivot 38. At the proximal end the two arms comprise forceps handles 30 and 32. The handles include a conventional ratchet 34. The handles are hinged at the pivot point 38. A box lock comprises the preferred hinge. Below the hinge 36 the instrument terminates in a jaw region 40.

The jaw region includes an upper jaw 42 and a lower jaw 44. Proximal the hinge is an aperture 46 formed by the upper and lower jaws. At the distal end of the jaw region each jaw forms a ring, as better seen in the plan views of FIGS. 4 and 5. A cup 56 is fastened to the ring of the lower jaw. The rings 52, 54 may be embossed with a pattern on their opposing surfaces if desired, to better enable them to grip tissue. The radial dimensions of the rings 52, 54 are oriented generally perpendicular to the plane of the aperture 46. At the hinge side of the aperture 46 the jaws are separated by a gap 48.

FIG. 5, which is a bottom view of the lower jaw 44, including the cup 56 and the ring 54 of the lower jaw, shows pins 58a–58c. These pins are press-fit or welded into holes around the cup 56, and project into the volume inside the cup. The cup is open on the bottom, as indicated at 50.

The purpose of the instrument of the present invention is to aid the surgeon in locating and forming the buttonhole 17 in conjunction with an intraluminal stapling instrument (ILS), such as that shown in U.S. Pat. No. 4,319,576 and commercially available from Ethicon, Inc., of Somerville, N.J. The first step is to determine the location of the buttonhole. The spacing between the buttonhole and side of the stomach along the lesser curvature determines the amount of stomach tissue at the bottom of the vertical pouch which is surrounded by the collar or band. This, of course, is the efferent stoma of the pouch. The first step in the formation of the pouch and stoma is to insert a 34 gauge gastric tube into the stomach, where the tube is aligned along the lesser curvature below the esophagus. The ILS anvil nut 74 and anvil 70 are fitted into the cup 56, as shown in FIG. 6, with the anvil surface 72 facing upward. The anvil nut 74 is provided about its periphery with a series of grooves or flutes 76. The alignment of the pins 58a–58c matches the pattern of the grooves 76 so that the pins extend into opposing grooves. The pins thus prevent the anvil nut 74 from rotating in the cup 56, and the pins also support the anvil nut in the cup. The anvil 70 is free to rotate when located in the cup.

The surgical instrument is then inserted into the abdominal cavity. The angulation of the instrument allows the instrument to be properly located without undue relocation of the stomach and in position to be conveniently engaged by the ILS. The lower jaw 44 with the cup 56 containing the anvil nut is placed posterior to the stomach, and the upper jaw 42 and ring 52 are applied to the anterior wall of the stomach. The cup 56 protects the anvil and nut from becoming dislodged in the abdominal cavity during insertion of the instrument. In this position, the gastric tube inside the stomach is contained within the aperture 46. The gap 48 between the jaws insures that no pinching engagement of the wall at the lesser curvature occurs, which could damage nerves and blood vessels in the stomach wall. The jaws are clamped shut, compressing the anterior and posterior walls of the stomach between the opposing surfaces of the rings 52 and 54. The ratchet 34 holds the closed instrument in place. The emplaced instrument is shown in FIG. 7, where the small pouch 100 is shown filling the aperture 46 and contains the gastric tube at this time.

When the instrument of the present invention is clamped in place as shown in FIG. 7, the anvil and anvil nut of the ILS are located beneath the ring 52 on the posterior side of the stomach. The ring 52 thus provides a target for locating the anvil and anvil nut. A Bovey cautery knife may then be used to perforate the posterior and anterior walls at the center of the ring 52. The central perforation will reveal the keyed hole in the center of the anvil 70. The shaft 88 of the ILS is inserted through the perforation so that the keyed, threaded end of the shaft 88 engages the keyed hole in the anvil and the succeeding anvil nut. As seen in FIG. 6, the threaded end of the shaft 88 is flattened on opposite sides to provide the keying. The ILS is then rotated to thread the shaft 88 into the anvil nut 74. The anvil 70 turns with the shaft due to the keying, but the anvil nut will not turn by reason of the pins 58a–58c that engage the grooves 76.

When the shaft 88 is fully tightened in the anvil nut 74, the ILS is adjusted to bring the staple-containing casing 80 against the anterior wall inside the ring 52. The adjusted ILS is then fired to affix two concentric rings of staples 84 through the stomach walls, and to cut a circular hole inside the staples with the ILS's cylindrical scalpel 82. By virtue of the secure clamping of the stomach walls by the ring 52 and 54, substantially no gastric secretions are allowed to seep or spill into the peritoneal cavity during the stapling and cutting procedure.

With the buttonhole now cut and stapled, the forceps ratchet 34 is disengaged to relax the clamping pressure. The anvil and anvil nut on the posterior side of the buttonhole may now be worked through the stapled circle. The anvil is of a slightly larger diameter than the buttonhole, but the buttonhole will stretch sufficiently so that the anvil may be worked carefully through the buttonhole. The entire ILS may then be removed from the jaws of the instrument.

In order to facilitate ILS removal, the angularity of the instrument was distributed over several bends. Ideally, it would be desirable to angle the central axis of the hinge and handle portions upward from the axis 60 of the jaw region 40 (see FIG. 3) at an angle of approximately 45°. This angle would allow the lesser curvature to be engaged by the instrument with little need to reorient the stomach in the abdominal cavity. However, it was found that the formation of such a large angle on the jaw side of the hinge 36 caused the rings 52, 54 to move together and apart at a significant angle relative to the axis of the ILS shaft 88. This relative lateral movement of the rings would entrap the casing 80 of the ILS, which could then not be withdrawn from the rings. This difficulty was solved by distributing the angularity of the instrument on either side of the hinge. In the preferred embodiment, the axis 62 of the hinge region is at a 30° angle relative to the jaw axis 60, and the central axis 64 of the handle portion is at a 15° angle relative to axis 62. It has been found that the distributed angularity still permits convenient approach and engagement of the stomach, while reducing the lateral component of the jaw motion sufficiently so that the ILS is not entrapped in the rings when the clamping pressure is released.

After the ILS has been removed from the rings 52, 54, the instrument is removed from the abdominal cavity. The buttonhole 17 may then be inspected for integrity and the procedure continued as described above.

It may thus be seen that the surgical instrument of the present invention serves numerous purposes during the vertical banded gastroplasty procedure. Specifically, the instrument (a) captures the gastric tube along the lesser curvature and holds it in place without damaging the neurovascular structures of the stomach wall; (b) protects the anvil nut from becoming dislodged in the abdominal cavity by enclosing it in the cup; (c) locates and holds the ILS nut and anvil against the posterior wall; (d) clamps the stomach walls where the buttonhole is to be formed; (e) properly locates the buttonhole site relative to the efferent stoma site; (f) provides a target for ILS perforation and insertion; (g) prevents the anvil nut from rotating while allowing the anvil to turn as the shaft is threaded into the nut; and (h) prevents gastric secretion contamination of the peritoneal cavity. The instrument may be conveniently made of stainless steel or of a disposable material.

What is claimed is:

1. A surgical instrument for use with a surgical stapling device comprising a pair of instrument arms each having a handle at one end, a jaw at the other end, and an intermediate region at which the arms are hinged together, said jaws each including an open ring-like structure, said ring-like structures opposing each other in substantially parallel planes when said jaws are closed to compress tissue, whereby said ring-like structures provide a guide for stapling the tissue compressed between the jaws and accessible inside said ring-like structures, wherein one of said jaws includes means for retaining a part of a surgical stapling device.

2. A surgical instrument for use with a surgical stapling device comprising a pair of instrument arms each having a handle at one end, a jaw at the other end, and an intermediate region at which the arms are hinged together, said jaws each including an open ring-like structure, said ring-like structures opposing each other in substantially parallel planes when said jaws are closed to compress tissue, whereby said ring-like structures provide a guide for stapling the tissue compressed between the jaws and accessible inside said ring-like structures, wherein said jaws further include opposing arcuate sections defining an aperture when said jaws are closed during use to surround tissue peripheral to the stapling site to thereby locate the stapling site with respect to said surrounded tissue, said aperture defined by said arcuate sections being located in a plane which is substantially perpendicular to said substantially parallel planes.

3. A surgical instrument comprising forceps handles, a hinge region, and a pair of jaws, said jaws including opposing arcuate sections proximal said hinge region, and said jaws including, at the proximal ends thereof, opposing ring-like structures for compressing tissue therebetween while leaving exposed tissue in the center of said ring-like structures, further comprising means, attached to one of said ring-like structures, for retaining a part of a surgical stapling device.

4. The surgical instrument of claim 1, wherein said retaining means comprises a cup-like structure connected to the ring-like structure of one of said jaws.

5. The surgical instrument of claim 4, wherein said part of a surgical stapling instrument includes a stapling anvil.

6. The surgical instrument of claim 2, wherein the arcuate sections are located intermediate said ring-like structures and said hinged region.

7. The surgical instrument of claim 6, further comprising a gap located between said jaws on the side of said aperture proximal said hinged region which prevents compression of said surrounded tissue by said instrument arms proximal said aperture.

8. The surgical instrument of claim 2, wherein said handles include a ratchet for clamping said arms in a closed position.

9. The surgical instrument of claim 3, wherein said opposing arcuate sections define an aperture therebetween, said aperture including a tapered gap proximal said hinge region.

10. A surgical instrument suitable for use in gastroplastic surgery and having a handle region, a jaw region, and an intermediate hinge region, and said jaw region comprising:

means for locating said instrument with reference to a tubular region of the stomach; and means for compressively defining a hole location on the stomach wall, said hole location bearing a predetermined relationship to the location of said tubular region, further comprising means for retaining a part of a surgical stapling device proximal said hole location.

* * * * *